US00PP07785P

United States Patent [19]

Meilland

[11] Patent Number: Plant 7,785

[45] Date of Patent: Feb. 11, 1992

[54] ROSE PLANT—MEIKIJI VARIETY

[75] Inventor: Alain A. Meilland, Antibes, France

[73] Assignee: The Conard-Pyle Company, West Grove, Pa.

[21] Appl. No.: 580,253

[22] Filed: Sep. 10, 1990

[51] Int. Cl.[5] ..... A01H 5/00

[52] U.S. Cl. ..... Plt./22

[58] Field of Search ..... Plt./1, 22

[56] References Cited

U.S. PATENT DOCUMENTS

P.P. 1,987 11/1960 Raffel ..... Plt. 22

P.P. 5,553 9/1985 Olij ..... Plt. 22

*Primary Examiner*—Howard J. Locker

*Attorney, Agent, or Firm*—Burns, Doane, Swecker & Mathis

[57] ABSTRACT

A new and distinct variety of Floribunda rose plant is provided which abundantly and continuously forms attractive long-lasting fully double bicolored blossoms. The blossoms are French Rose edged and suffused with Rose Bengal. The plant exhibits vigorous vegetation, is well-balanced, is semi-erect, and exhibits a relatively quick blooming cycle. The new variety is particularly well suited for the decoration of parks and gardens. Good resistance to cryptogamic diseases also is exhibited.

1 Drawing Sheet

SUMMARY OF THE INVENTION

The new variety of Floribunda rose plant was created by artificial pollination wherein two parents were crossed which previously had been studied in the hope that they would contribute the desired characteristics. The female parent (i.e., the seed parent) of the new variety was the Meicadol variety (nonpatented in the United States). The male parent (i.e., the pollen parent) of the new variety was the Magic Carrousel variety (U.S. Plant Pat. No. 3,601). The parentage of the new variety can be summarized as follows:

Meicadol × Magic Carrousel.

The seeds resulting from the above pollination were sown and 38 small plants were obtained which were physically and biologically different from each other. Selective study resulted in the identification of a single plant of the new variety.

The new variety meets well the needs of the horticultural industry for all uses, and is particularly well suited for growing in parks and gardens. Well-balanced plants are formed which are semi-erect and bloom profusely and continuously in relatively quick cycles.

It was found that the new variety of Floribunda rose plant of the present invention possesses the following combination of characteristics:

(a) forms abundantly and continuously attractive long-lasting bicolored double blossoms which are French Rose edged and suffused with Rose Bengal,
(b) forms medium green adult wood,
(c) forms vigorous vegetation,
(d) is particularly well suited for the decoration of parks and gardens, and
(e) is not particularly affected by cryptogamic diseases.

The new variety has been found to undergo asexual propagation by a number of conventional routes, including budding, grafting, and cuttage. Asexual reproduction by the above mentioned methods as performed in France shows that the characteristics of the new variety are strictly transmissible from one generation to another and appear to be firmly fixed.

The new variety has been named the Meikiji variety.

BRIEF DESCRIPTION OF PHOTOGRAPH

The accompanying photograph shows as nearly true as it is reasonably possible to make the same, in a color illustration of this character, typical specimens of the plant parts of the new variety. The rose plants of the new variety were three years of age and were observed during June while budded on *Rose froebelli* understock and growing outdoors at LeCannet-des-Maures, Var, France.

DETAILED DESCRIPTION

Figures 1, 2, 3, 4, 5, 6, 7, 8, 9, 10, 11, 12, 13, 14, 15, 16:
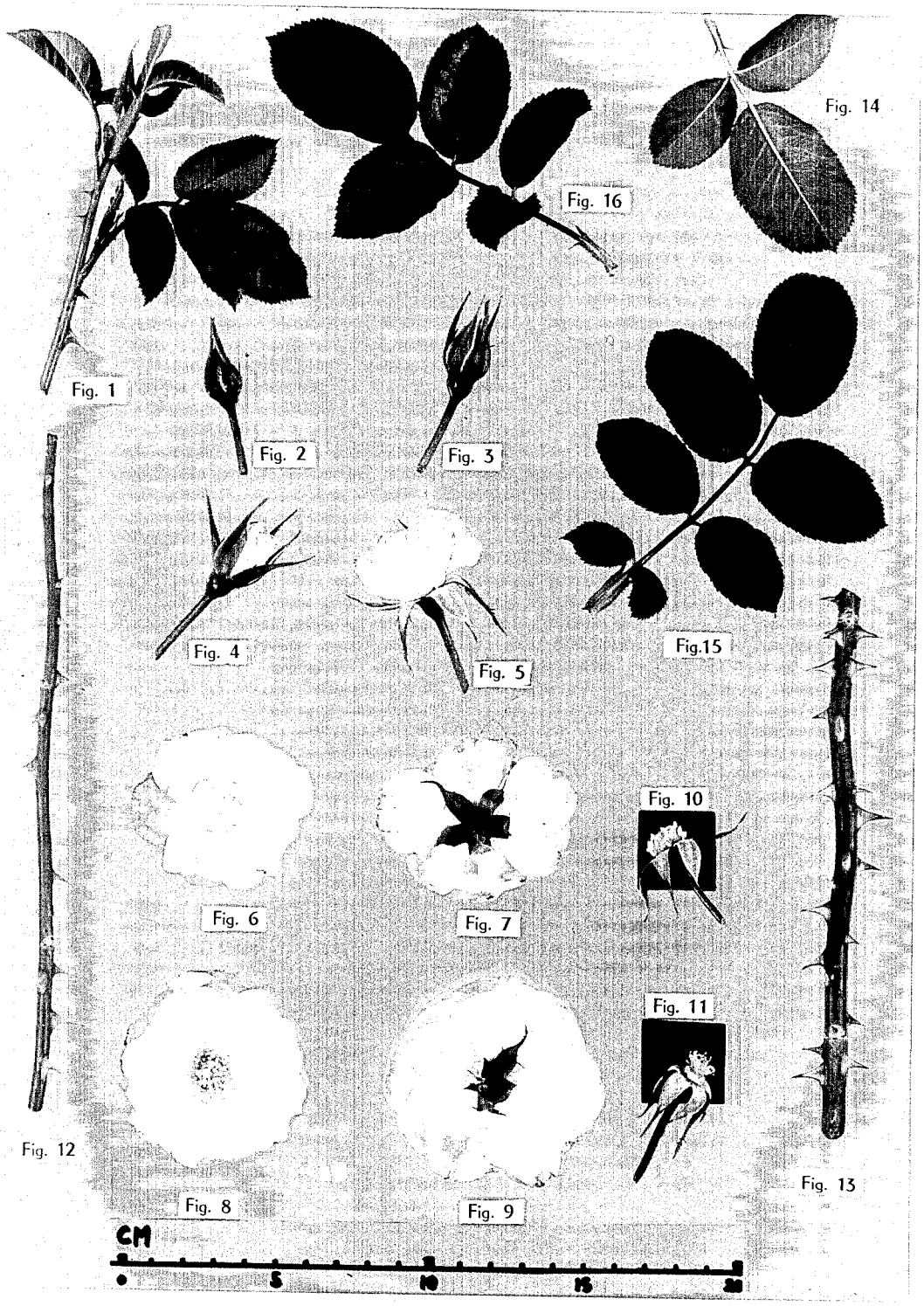
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of an open flower — plan view — obverse.
FIG. 7 illustrates a specimen of an open flower — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of an adult main branch.
FIG. 14 illustrates a specimen of a leaf with three leaflets — under surface.
FIG. 15 illustrates a specimen of a leaf with seven leaflets — upper surface.
FIG. 16 illustrates a specimen of a leaf with five leaflets — upper surface.

The chart used in the identification of the colors is that of The Royal Horticultural Society (R.H.S. Colour Chart). The terminology which precedes reference to the chart has been added to indicate the corresponding color in more common terms. The description is based on three year old specimens of the new variety during June while budded on *Rosa froebelli* understock and growing outdoors at LeCannet-des-Maures, Var, France.

Class: Floribunda.

Plant:

*Height.*—Approximately 90 cm. on average at the end of the growing season.

*Habit.*—Semi-erect.

Branches:

*Color.*—Young stems: lettuce green, Yellow-Green Group 144A, more or less stained with reddish coloration. Adult wood: medium green, Yellow-Green Group 146B.

*Thorns.*—Size: large. Quantity: numerous. Color: pinkish with greenish tips on young stems, and greenish changing to tan on adult wood Leaves:

*Stipules.*—Adnate, pectinate, narrow and linear.

*Petioles.13* Upper surface: reddish brown on young foliage anbd medium green on adult foliage with more or less glandular edges. Under surface: medium green, with a few prickles.

*Leaflets.13* Number: 3, 5, and 7. Shape: oval. Serration: single and regular. Texture: consistent. General appearance: foliage is dense and bright. Color (young foliage): Upper surface: bronze green, Yellow-Green Group 146A, and more or less edged with reddish brown. Under surface: light green, Yellow-Green Group 146C, and more or less stained with reddish brown. Color (adult foliage): Upper surface: dark green, Yellow-Green Group 147A. under surface: light green, Yellow-Green Group 147C.

Inflorescence:

*Number of flowers.*—Commonly 1 to 5 per stem.

*Peduncle.*—Short, light green, more or less glandular and tinged with reddish coloration, approximately 3 cm. in length on average.

*Sepals.*—Upper surface: tomentose and greenish in coloration. Under surface: medium green, more or less stained with reddish coloration, and the outer sepals have glandular edges that are slightly appendiculated.

*Buds.*—Shape: oval. Length: approximately 2.5 to 3 cm on average. Size: medium. Color upon opening: Upper surface: pale Orient Pink, Red Group 36D, with a white center and edged with dark venetian pink, Red Group 49A. Under surface: pale Orient Pink, Red Group 36D, more or less shaded with Rose Bengal, Red-Purple Group 57B.

*Flower.*—Shape: flat cup, double. Diameter: approximately 7 to 10 cm. on average. Color (when opening begins): Upper surface: pale Neyron Pink, Red Group 55 D, with a white center and more or less stained and edged with dark Rose Bengal, Red-Purple Group 57A. Under surface: pale Orient Pink, Red Group 36D. and more or less stained and edged with Rose Bengal, Red-Purple Group 57A. Color (when blooming): Upper surface: French Rose, Red Group 49D, more or less edged and suffused with Rose Bengal, Red-Purple Group 57D. under surface: pale Orient Pink, Red Group 36D, turning slightly white and edged and suffused with light Rose Bengal, Red-Purple Group 57D. Color (at end of opening): Upper surface: French Rose, Red Group 49D, turning white, and more or less edged and suffusedw tih light rose Bengal, Red-Purple Group 57D. Under surface: pale Orient Pink, Red Group 36D, turning white, and lightly edged and suffused with light Rose Bengal, Red-Purple Group 57D. Fragrance: none. Lasting quality: long lasting blossoms. Petal drop: good. Petal number: approximately 25 to 30 on average. Petal texture: consistent. Petal form: rounded to oval. Stamen number: approximately 58 on average. Anthers: normal, golden yellow in coloration. Filaments: bright yellow widely stained with orange, and of irregular heights. Pistils: approximately 137 on average. Stigmas: normal. Styles: greenish yellow, and of irregular heights. Receptacle: medium green, smooth, and in longitudinal section in the shape of a pitcher.

Development:

*Vegetation.*—Vigorous and strong.

*Blooming.*—Very abundant and continuous.

*Aptitude to bear fruit.*—Poor.

*Resistance to frost.*—Very good.

*Resistance to diseases.*—Good.

I claim:

1. A new and distinct variety of Floribunda rose plant characterized by the following combination of characteristics:

(a) forms abundantly and continuously attractive long-lasting bicolored double blossoms which are French Rose edged and suffused with Rose Bengal, (b) forms medium green adult wood, (c) forms vigorous vegetation, (d) is particularly well suited for the decoration of parks and gardens, and (e) is not particularly affected by cryptogamic diseases;

substantially as herein shown and described.

* * * * *

CM
0
5
10
15
20